(12) United States Patent
Patel et al.

(10) Patent No.: US 12,171,960 B2
(45) Date of Patent: Dec. 24, 2024

(54) VENTRICULAR UNLOADING SYSTEM

(71) Applicant: ABBOTT CARDIOVASCULAR SYSTEMS INC., Santa Clara, CA (US)

(72) Inventors: Samir Patel, Mountain View, CA (US); Emmanuel Darzins, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 217 days.

(21) Appl. No.: 17/491,390

(22) Filed: Sep. 30, 2021

(65) Prior Publication Data

US 2022/0203072 A1 Jun. 30, 2022

Related U.S. Application Data

(60) Provisional application No. 63/131,265, filed on Dec. 28, 2020.

(51) Int. Cl.
| | | |
|---|---|---|
| *A61M 25/00* | (2006.01) | |
| *A61M 25/06* | (2006.01) | |
| *A61M 60/174* | (2021.01) | |
| *A61M 60/279* | (2021.01) | |

(52) U.S. Cl.
CPC .... *A61M 25/0606* (2013.01); *A61M 25/0074* (2013.01); *A61M 60/174* (2021.01); *A61M 60/279* (2021.01); *A61M 2025/0002* (2013.01); *A61M 2205/3334* (2013.01);
(Continued)

(58) Field of Classification Search
CPC .......... A61M 25/0606; A61M 25/0074; A61M 60/174; A61M 60/279; A61M 2025/0002; A61M 2205/3334; A61M 2210/125; A61M 2230/06; A61M 2230/30; A61M 1/3655; A61M 1/3659; A61M 60/232; A61M 60/531; A61M 60/585; A61M 60/117
See application file for complete search history.

(56) References Cited

U.S. PATENT DOCUMENTS 3,680,544 A * 8/1972 Shinnick ................ A61M 25/10
600/581
3,952,742 A * 4/1976 Taylor ................ A61M 25/1011
604/21
(Continued)

FOREIGN PATENT DOCUMENTS

WO 2020081835 A1 4/2020

*Primary Examiner* — Robert J Utama
*Assistant Examiner* — Hamza A Darb
(74) *Attorney, Agent, or Firm* — WOMBLE BOND DICKINSON (US) LLP (57) ABSTRACT

A system and method of unloading a heart chamber is described. The chamber can be a ventricle and the system can unload the ventricle during or after a heart attack. The ventricular unloading system includes a transthoracic needle insertable into the ventricle, a vascular access cannula insertable into a blood vessel, and a pump to move blood from the ventricle to the blood vessel through the transthoracic needle and the vascular access cannula. The ventricular unloading system can be used by an emergency medical technician in a non-hospital setting. Accordingly, the ventricular unloading system can provide early protection against infarct to improve clinical outcomes for a patient. Other embodiments are also described and claimed.

19 Claims, 6 Drawing Sheets

(52) U.S. Cl.
CPC ... *A61M 2210/125* (2013.01); *A61M 2230/06* (2013.01); *A61M 2230/30* (2013.01)

(56) References Cited

U.S. PATENT DOCUMENTS

| | | | |
|---|---|---|---|
| 2002/0128587 A1* | 9/2002 | Aboul-Hosn | A61M 60/531 |
| | | | 604/7 |
| 2003/0191357 A1 | 10/2003 | Frazier | |
| 2006/0224110 A1* | 10/2006 | Scott | A61M 1/3659 |
| | | | 604/95.01 |
| 2010/0121133 A1* | 5/2010 | Schumer | A61M 60/531 |
| | | | 600/17 |
| 2019/0216995 A1 | 7/2019 | Kapur et al. | |

\* cited by examiner

VENTRICULAR UNLOADING SYSTEM

This application claims the benefit of priority of U.S. Provisional Patent Application No. 63/131,265, filed on Dec. 28, 2020, entitled "Ventricular Unloading System," and that application is incorporated herein by reference in its entirety to provide continuity of disclosure.

BACKGROUND

Field

The present disclosure relates to systems and methods for percutaneous ventricular interventions. More specifically, the present disclosure relates to systems for percutaneously unloading a ventricle of a heart.

BACKGROUND INFORMATION

Heart attacks can occur when a coronary artery becomes obstructed. The arterial obstruction can cause acute myocardial infarction (AMI) when reduced blood flow results in a lack of oxygen supply to the myocardium, and thus, myocardial damage. Arterial occlusion is not the only determinant of myocardial damage, however. A degree of collateral blood flow, presence of multivessel disease, micovasculature dysfunction, or system hypotension can also contribute to AMI. Essentially, any factor that reduces blood flow to the myocardium can worsen ischemic injury.

Myocardial damage may also be affected by an oxygen demand of the pumping heart muscle. Heart rate, ventricular wall stress, ventricular systolic pressure, ventricular diastolic pressure, and ventricular stroke work are all variables that affect myocardial oxygen demand. When these variables increase, myocardial oxygen demand increases. More particularly, these variables indicate ventricular load, and as ventricular load increases so does myocardial oxygen demand. Higher ventricular load, in the presence of reduced oxygen supply, can contribute to myocardial damage during a heart attack.

Myocardial damage is perilous to a patient. For every 5% increase in myocardial infarct size, one-year all-cause mortality increases by 19%. Similarly, for every 5% increase in myocardial infarct size, heart failure hospitalization increases by 20%. Accordingly, the reduced myocardial oxygen supply or increased ventricular load experienced during a heart attack can put the patient at future risk.

SUMMARY

Existing heart attack treatments aim to increase myocardial oxygen supply. For example, percutaneous coronary intervention (PCI) can be used to improve blood flow in an occluded coronary vessel. Such procedures require hospitalization and surgery, however, and myocardial damage may occur beforehand, e.g., en route to the hospital. Accordingly, current treatments that seek to improve outcomes by increasing myocardial oxygen supply are unable to be deployed in non-hospital settings and do not address the other contributor to myocardial damage: ventricular load.

A ventricular unloading system is provided. In an embodiment, the ventricular unloading system includes a transthoracic needle that can be inserted into a ventricle of a heart, and a vascular access cannula that can be inserted into a blood vessel. The transthoracic needle can be coupled to the vascular access cannula by a fluid transfer network. For example, a pump can have an inlet coupled to the transthoracic needle via an inlet line and an outlet coupled to the vascular access needle via an outlet line such that the pump can move blood from the heart to the blood vessel. More particularly, a controller can receive sensed information about a ventricular load of the heart, and control the pump to pump blood from the transthoracic needle disposed in a ventricle of the heart to the vascular access cannula disposed in the blood vessel. Accordingly, the system can unload the ventricle to reduce a likelihood of myocardial damage.

The pump can be controlled to pump the blood at a pump rate based on the ventricular load. For example, the sensed information about the ventricular load can include one or more of a heart rate, a ventricular wall stress, a systolic pressure, a diastolic pressure, or a stroke work of the ventricle. When any of this information indicates that the ventricular load is too high, e.g., when the systolic pressure is above 12 mm Hg, the pump rate can be increased to unload the ventricle more.

The sensed information can be provided by sensors distributed throughout the system. For example, the transthoracic needle can include a transthoracic needle sensor to sense information about the ventricular load. Alternatively or additionally, the outlet line or the vascular access cannula can include a sensor that senses pressure within the blood vessel. Accordingly, the controller can receive several signals generated by system sensors and, in response, output pump control parameters that are used by a motor portion of the pump to pump blood and unload the ventricle.

A method of using the ventricular unloading system to reduce ventricular load is provided. A non-transitory computer-readable medium storing instructions is also provided. The instructions, when executed by one or more processors of the ventricular unloading system, cause the ventricular unloading system to perform the method. In an embodiment, the method includes receiving the sensed information about the ventricular load of the heart, and controlling the pump to operate at a pump rate based on the ventricular load.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments describe a ventricular unloading system. The ventricular unloading system may be used to redirect blood from a ventricle in a non-hospital setting to reduce ventricular load and therefore reduce infarct size sustained by a patient from a heart attack. Alternatively, the ventricular unloading system may be used in other applications, such as to redirect blood from another heart chamber, such as an atrium. Thus, reference to the system as being a ventricular unloading system is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a needle. Similarly, "proximal" may indicate a second direction opposite to the first direction. Such terms are provided to establish relative frames of reference, however, and are not intended to limit the use or orientation of a ventricular unloading system to a specific configuration described in the various embodiments below.

In an aspect, a ventricular unloading system is provided. The system can include a transthoracic needle for insertion into a left ventricle and a vascular access cannula for insertion into a blood vessel. The system can also include a pump to remove blood from the left ventricle through the transthoracic needle and redirect the blood into the blood vessel through the vascular access cannula. The redirected blood can reduce oxygen demand of the myocardium by decreasing its work load. Advantageously, the method of using the ventricular unloading system to reduce the ventricular load can be performed by an emergency medical technician in a non-hospital setting, e.g., while en route to a hospital, and prior to the administration of percutaneous coronary intervention (PCI). Accordingly, the ventricular unloading system can provide the patient with early protection against infarct and, thus, potentially improve one-year all-cause mortality and heart failure outcomes.

Figure 1:
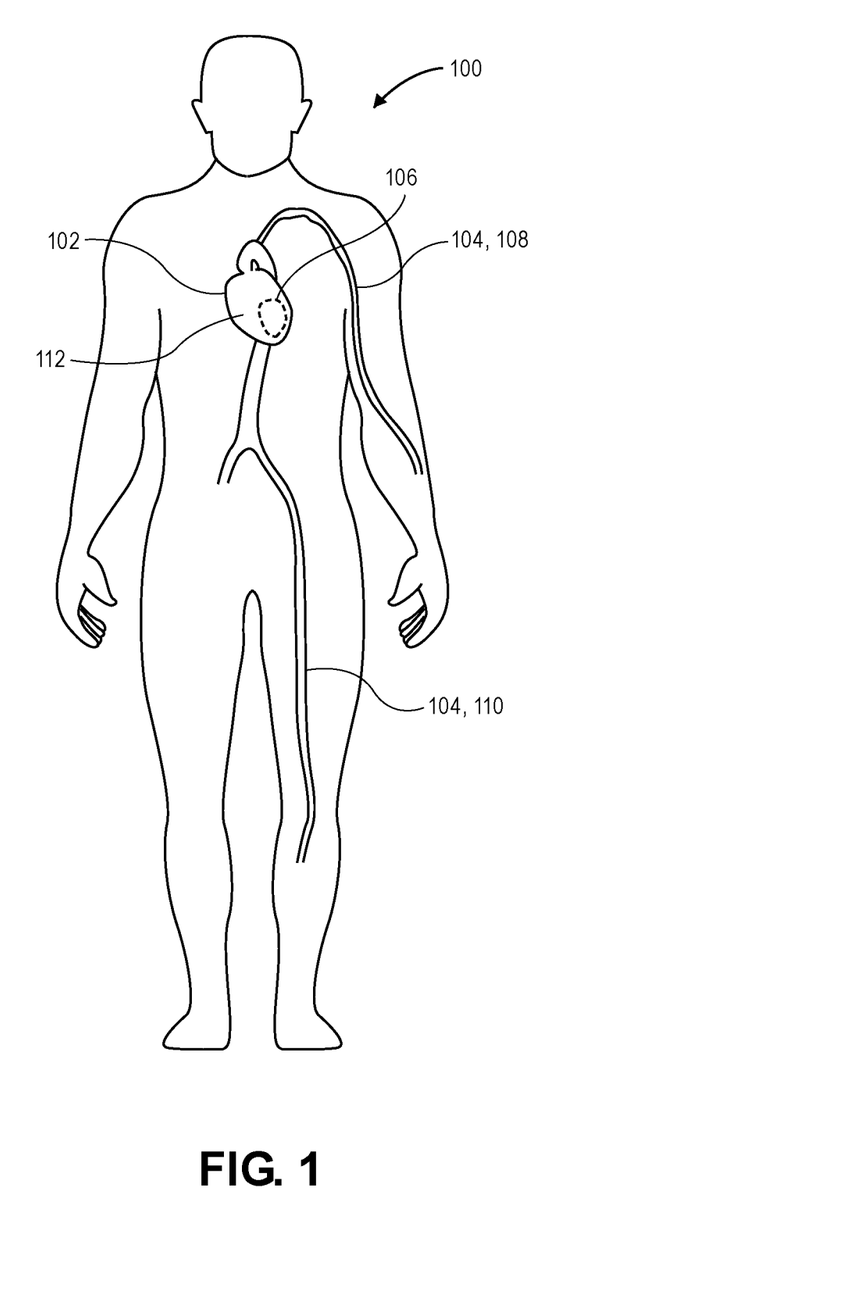
FIG. 1 is a pictorial view of a patient anatomy, in accordance with an embodiment.

Referring to FIG. 1, a pictorial view of a patient anatomy is shown in accordance with an embodiment. A patient 100 has a vascular system, including a heart 102 and several blood vessels 104, including arteries and veins. The heart 102 includes several chambers, such as a left ventricle 106, which normally pump blood from the heart 102 to the blood vessels 104. For example, the left ventricle 106 pumps blood to a radial artery 108 and a femoral artery 110 of the patient 100. More particularly, the heart muscle, i.e., myocardium 112, contracts to squeeze blood out of the left ventricle 106 to the blood vessels 104.

The myocardium 112 requires blood to perform the pumping action. In particular, the myocardium 112 demands oxygen provided by such blood, and thus, the myocardial function depends on coronary arteries that feed blood to the myocardium 112. The coronary arteries may become clogged, however, reducing blood flow and oxygen supply to the myocardium 112. When this occurs, a heart attack can result. During the heart attack, ventricular load may remain high, even though myocardial capability is reduced. Increases in variables such as heart rate, ventricular wall stress, ventricular systolic and diastolic pressure, or ventricular stroke work can increase the ventricular load. Under the conditions of reduced myocardial oxygen supply and high ventricular load, acute myocardial infarction (AMI) can result.

Figure 2:
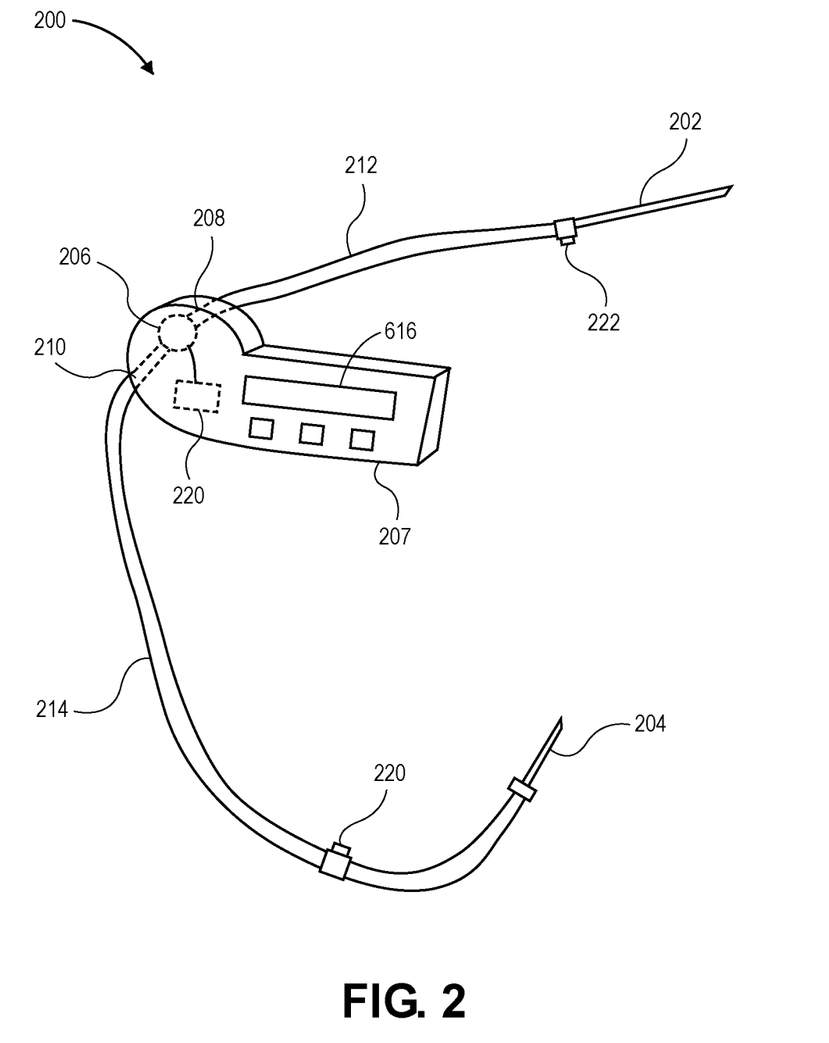
FIG. 2 is a perspective view of a vascular unloading system, in accordance with an embodiment.

Referring to FIG. 2, a perspective view of a vascular unloading system is shown in accordance with an embodiment. A ventricular unloading system 200 can be used to reduce the ventricular load of the heart 102. For example, the ventricular unloading system 200 can be used by an emergency medical technician to safely and quickly move, e.g., pump, blood from the left ventricle 106 into the blood vessel 104 during or after the heart attack. The ventricular unloading system 200 can therefore match the oxygen needs of the ventricle with the oxygen supply to the ventricle. This load matching can effectively reduce infarct size. Beneficially, reduced infarct size can lead to better clinical outcomes for the patient 100.

In an embodiment, the ventricular unloading system 200 includes a transthoracic needle 202. The transthoracic needle 202 may be adapted for insertion into the left ventricle 106 of the heart 102. For example, the transthoracic needle 202 may be guided by ultrasound to access the left ventricle 106 transthoracically by an emergency medical technician. The transthoracic needle 202 can include a thin-walled hypotube structure, including a tubular wall having an outer wall surface and an inner wall surface that defines a central lumen. The tubular wall can have a cross-sectional shape that is circular, oval, or any other shape that facilitates access to the ventricle via puncture, and blood transfer through the system 200, as described below.

The ventricular unloading system 200 also includes a vascular access cannula 204. The vascular access cannula 204 may be adapted for insertion into the blood vessel 104, e.g., the radial artery 108 or the femoral artery 110. For example, the vascular access cannula 204 may be a needle inserted into the blood vessel 104 under visual or ultrasound guidance by the emergency medical technician. Alternatively, the vascular access cannula 204 can be a catheter or cannula that is inserted into the blood vessel 104 using a standard vascular access approach.

The needles and/or cannulas 202, 204 can be sized to provide blood flow through the system 200 that meets the ventricular unloading demands of the method described below. For example, the needles and/or cannulas 202, 204 may be sized to provide blood flow through the system 200 in a range of 1-5 liters per minute. Such flow may be achieved using needles and/or cannulas 202, 204 having sizes in a range of 14-17 French. For example, it is contemplated that a transthoracic needle 202 and a vascular access cannula 204 having a size of 14 French can pass blood flow of 1-4 liters per minute. In an embodiment, the needles and/or cannulas 202, 204 are similarly sized. For example, both access elements can be 14 French needles and/or cannulas. Alternatively, the needles and/or cannulas 202, 204 may be differently sized. For example, the vascular access cannula 204 can have a larger size, e.g., 17 French, than the transthoracic needle 202 (which can have a size of 14 French, for example). Sizing of the needles and/or cannulas may be appropriate to the target anatomy. For example, the transthoracic needle 202 can be a large bore needle sized for insertion into the left ventricle 106 by a transthoracic approach, and the vascular access cannula 204 can be a catheter or cannula sized for insertion into an artery. Accordingly, needle and/or cannula size can be selected based on one or more of the target anatomy or the blood flow requirements of the ventricular unloading system 200.

Each of the needles/cannulas 202, 204 can be connected to respective lines. More particularly, the transthoracic needle 202 can be connected to an inlet line 212 and the vascular access cannula 204 can be connected to an outlet line 214. The lines can carry blood between the needles/cannulas 202, 204 and a pump 206. As shown, the pump 206 can be a component of a console 207. That is, the pump 206 can be mounted within a housing of the console 207. The lines can connect their respective vascular access elements to the pump 206. In an embodiment, the lines 212, 214 are medical grade tubing. For example, the lines may be PVC tubing lines. The tubing can include a biocompatible coating applied to an interior surface of the tubing lumen to reduce a likelihood of blood contamination as the blood passes through the system 200.

The housing of the console 207 can be an enclosure that contains several components, including the pump 206 and a controller 220 used to control the pump 206. The controller 220 can include circuitry, e.g., one or more processors and/or memory, to generate control parameters for driving the pump 206. It will be appreciated that the pump 206 as referred to herein can include a motor portion and a pump portion. The motor portion can be controlled by the controller 220 to drive the pump portion such that a desired flow rate is achieved within the tubing that transfers blood from the heart 102 to the blood vessel 104.

The pump 206 can connect the transthoracic needle 202 to the vascular access cannula 204. More particularly, the pump 206 can include an inlet 208 coupled to the transthoracic needle 202 through the inlet line 212, and an outlet 210 coupled to the vascular access cannula 204 through the outlet line 214. The pump 206 can operate to move blood from the ventricle 106 through the transthoracic needle 202 and the inlet line 212 to the inlet 208. The pump 206 can also move blood from the inlet 208 through the outlet 210 and the outlet line 214 to the vascular access cannula 204. Thus, the pump 206 can redirect blood, which would otherwise be pumped by the ventricle 106, from the ventricle 106 to the blood vessel 104. Accordingly, the pump 206 can perform some work of the ventricle 106, and thereby reduce the ventricular load.

The pump 206 can be a compact mobile pump that is deployable in the field, e.g., in a non-hospital setting. The pump 206 may be any pump type that is safe to place in communication with the vascular system. For example, the pump 206 may be a peristaltic pump, such as pumps used in heart-lung machines, or a centrifugal heart pump, which can safely circulate blood from the ventricle 106 to the blood vessel 104.

As described below, one or more of the transthoracic needle 202 or the vascular access cannula 204 can include sensors to sense information about the environment, e.g., about pressure within the ventricle 106 or the blood vessel 104. Alternatively, or additionally, the pump 206 can include sensors to detect similar information (not shown). For example, the pump 206 can include a transducer at the inlet 208 and/or the outlet 210 to sense blood pressure entering the pump 206 (corresponding to the ventricle pressure) and/or blood pressure leaving the pump 206 (corresponding to the blood vessel pressure). The transducers can provide hemodynamic parameters related to the blood flow that may be used to control the pump 206 to effectively manage pressure of the heart 102 and the vascular system. This pressure management is achieved while the pump 206 pulls blood from the ventricle 106 to the blood vessel 104 to unload the ventricle 106.

As described above, the controller 220 may be incorporated into a housing of the console 207. Alternatively, the controller 220 may be physically separate from, and in communication with, the pump 206 to control the pumping action. For example, the controller 220 may be embodied as application software running on a tablet computer that is wirelessly connected to the console 207. Accordingly, the controller 220 can receive user inputs through the peripheral device and signals from the sensors and, based on inputs generate output control parameters to drive the pump 206.

In an embodiment, the controller 220 includes one or more processors (FIG. 6) to control the pump 206 to move blood from the transthoracic needle 202 to the vascular access cannula 204 based on the sensed information about the ventricular load. For example, the transthoracic needle 202 can be disposed in the ventricle 106 and vascular access cannula 204 can be disposed in the blood vessel 104, and the controller 220 can control a pump rate of the pump 206. The pump rate can determine the flow rate of blood from the ventricle 106 to the blood vessel 104 through the needles/cannulas 202, 204.

The controller 220 can control the pump 206 based on sensed information about the ventricular load of the heart 102. For example, as described below, the ventricular unloading system 200 can include one or more sensors to sense information about the patient 100 or the pumping process. The sensors can generate signals corresponding to the sensed information, and transmit the signals to the controller 220 through a wired or wireless connection. More particularly, the sensors may be connected directly to electrical contacts of the controller, or alternatively, the sensors may be connected to a relay device that sends the generated signals (pre- or post-processed) to the controller 220.

In an embodiment, the controller 220 can receive the sensed information from the sensor(s), and can control the pump 206 based on the sensed information. For example, the sensor(s) can sense information about the ventricular load of the heart 102, and one or more processors of the controller 220 can determine the pump rate based on the sensed information, and drive the pump 206 accordingly. The sensed information can include information about any variable that affects the ventricular load. For example, the sensed information can include one or more of a heart rate, a ventricular wall stress, a systolic pressure, a diastolic pressure, or a stroke work of the ventricle 106.

The console 207 can house, in addition to the pump 206 and controller 220, additional components to facilitate operation of the system. A power source, such as a battery or an external electrical connector, can be incorporated within the console 207 to provide power to the pump 206 (i.e., the motor portion of the pump) and/or controller 220. The console 207 can include one or more input and/or output elements. For example, the console 207 can include a display to present information about the ventricular unloading process to a user. Such information may include a pump speed, a blood flow rate, blood pressure within the system needles and/or cannulas, etc. The console 207 may also include one or more buttons to receive user inputs for controlling the process. For example, the buttons can include a button to receive a user input to increase pump speed, decrease pump speed, etc. Various components of the system 200, which may be incorporated within the console 207, are described below with respect to FIG. 6.

Figure 3:
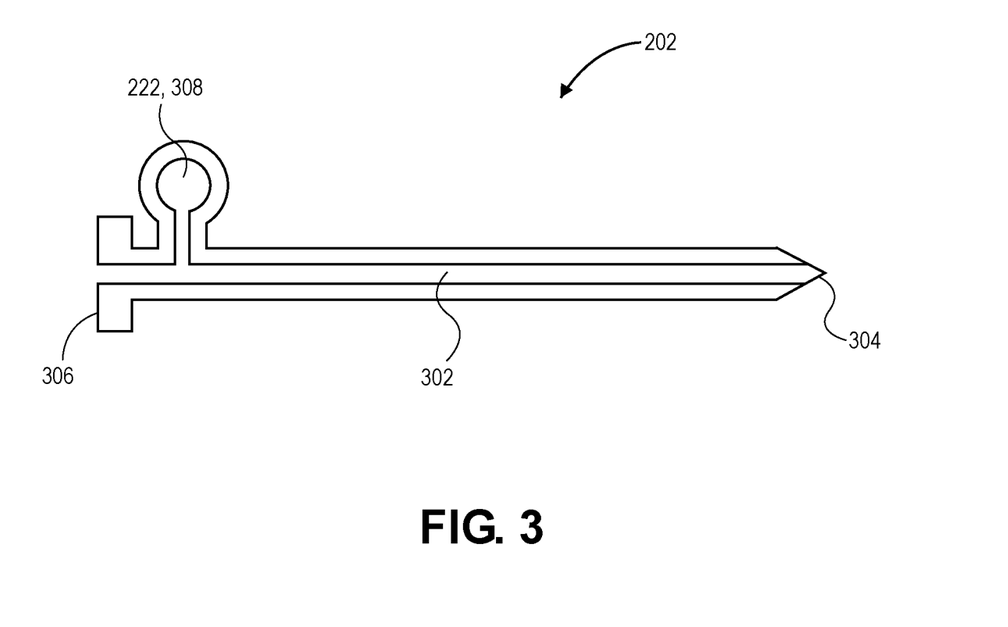
FIG. 3 is a sectional view of a transthoracic needle, in accordance with an embodiment.

Referring to FIG. 3, a sectional view of a transthoracic needle is shown in accordance with an embodiment. The transthoracic needle 202 includes a transthoracic needle lumen 302 extending axially from a proximal hub 306 to a distal tip 304. The transthoracic needle 202 can be a large bore needle, e.g., a 14 French needle, having the distal tip 304 adapted to puncture the patient 100 for insertion into the left ventricle 106. The proximal hub 306 can be adapted to connect to the inlet line 212. For example, the proximal hub 306 can include a Tuohy-Borst adapter to allow the transthoracic needle 202 to be fastened to a mating adapter on the inlet line 212.

In an embodiment, the transthoracic needle 202 includes one or more sensors 222. For example, the transthoracic needle 202 can include a transthoracic needle sensor 308 to sense information about the ventricular load. More particularly, the transthoracic needle sensor 308 can detect any variable that directly or indirectly correlates with the ventricular load. For example, the transthoracic needle 202 can be a pressure sensor. The pressure sensor can include a piezo-electrical/resistive sensor or an optical sensor. Accordingly, the transthoracic needle 202 can sense the pressure of blood within the transthoracic needle lumen 302, and the blood pressure can be used by the processor(s) of the controller 220 to determine ventricular pressure, heart rate, or another variable affecting ventricular load for use in controlling the pump 206.

The transthoracic needle 202 can include structure to support increased flow from the ventricle 106 to the blood vessel 104. For example, the distal tip structure of the transthoracic needle 202 can include a distal tip dilator (not shown). The distal tip dilator can increase the volume of blood flow through the transthoracic needle 202 to reach the flow requirements for ventricular unloading.

In an embodiment, the sensors 222 include a transthoracic sensor mounted on inlet line 212. The sensor may be a flow sensor to detect blood flow through the line. Alternatively, the sensor may be a pressure sensor adapted to sense blood pressure within the line. Accordingly, it will be appreciated that system 200 can include several sensors 222 distributed throughout the system components, including on the needle 202, line 212, line 214, and/or cannula 204.

The transthoracic needle 202 may also include, or be integrated with, a vessel closure unit. In an embodiment, the vessel closure unit can include a suture-mediated closure device, and the sutures of the vessel closure unit can be deployed around the transthoracic needle 202 at the myocardial puncture site of the heart 102 and/or at the puncture site of the chest of the patient 100. Alternatively, the vessel closure unit can include a plug or grommet-mediated closure device. The device can deploy a permanent or biodegradable plug into the puncture path, e.g., in the myocardium 112 or the chest. The vessel closure unit can achieve hemostasis of the puncture path after removing the transthoracic needle 202, e.g., following the ventricular unloading procedure.

As an alternative, or in addition to, integrating a vessel closure unit with the transthoracic needle 202, the puncture path may be pre-closed. For example, sutures may be inserted around the entry point of the puncture path, and the needle 202 may be passed through the sutures. Accordingly, upon completion of the access procedure, the transthoracic needle 202 can be removed and the sutures can be tied to provide a suture-mediated closure of the access wound.

The vascular access cannula 204 can have a structure similar to the transthoracic needle 202. For example, the vascular access cannula 204 may have a same lumen size, e.g., 14 French. In an embodiment, the vascular access cannula 204 includes a vascular access cannula lumen extending axially from a proximal hub to a distal tip. The proximal hub can be adapted to connect to the outlet line 214. For example, the proximal hub can include a Tuohy-Borst adapter to allow the vascular access cannula 204 to be fastened to a mating adapter on the outlet line 214. Like the transthoracic needle 202, the vascular access cannula 204 can include one or more sensors. For example, the vascular access cannula 204 can include a vascular access cannula sensor 220, on cannula 204 or line 220, to sense information about the blood vessel 104. More particularly, the vascular access cannula 204 can have a pressure sensor to sense the pressure of blood within the vascular access cannula lumen. Accordingly, the vascular access cannula sensor 220 can sense information about the vessel pressure, i.e., the pressure of blood within the blood vessel 104, and the vessel pressure can be used by the processor(s) of the controller 220 to control the pump 206.

The vascular access cannula sensor 220 can include other sensors to monitor and control the ventricular unloading process. For example, a flow sensor integrated with the return line 214 to detect blood flow there through. The flow sensor can be an ultrasonic flow sensor that is externally mounted on the tubing. Alternatively, the flow sensor can be internal to the tubing lumen. In any case, the flow sensor can generate signals that are provided to the controller 220 to measure how much blood flow is returning to the patient. The controller 220 may determine, based on such measurements, whether to increase or decrease blood flow through the system 200, and drive the pump 206 accordingly.

Figure 4:
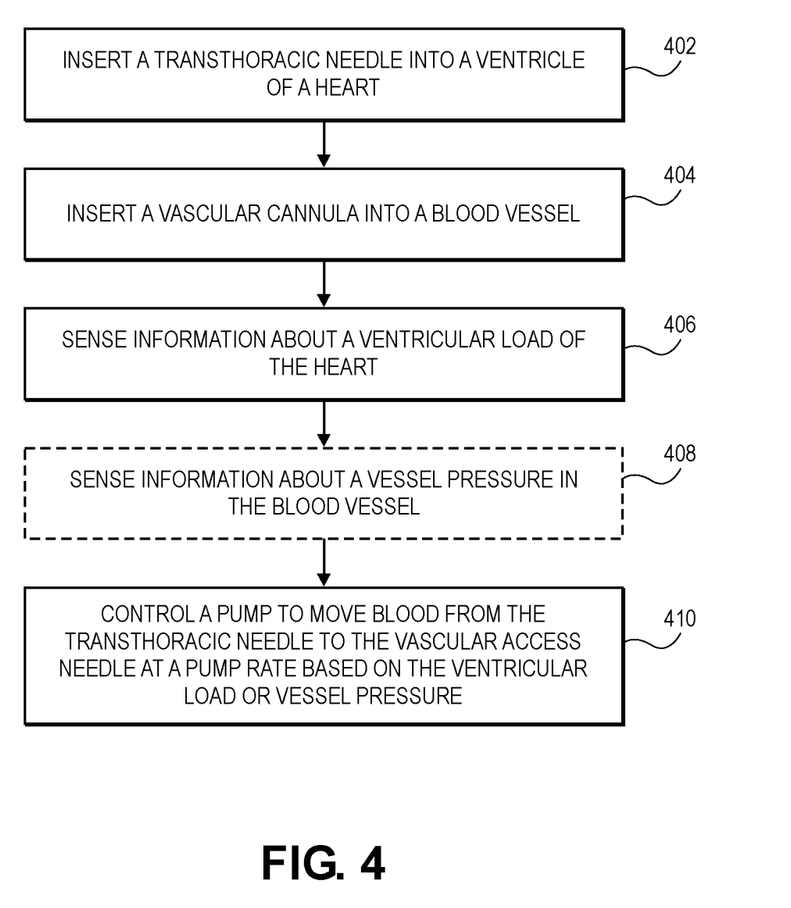
FIG. 4 is a flowchart of a method of using a vascular unloading system, in accordance with an embodiment.

Referring to FIG. 4, a flowchart of a method of using a vascular unloading system is shown in accordance with an embodiment. Advantageously, the method can be performed outside of a hospital by an emergency medical technician.

Figure 5:
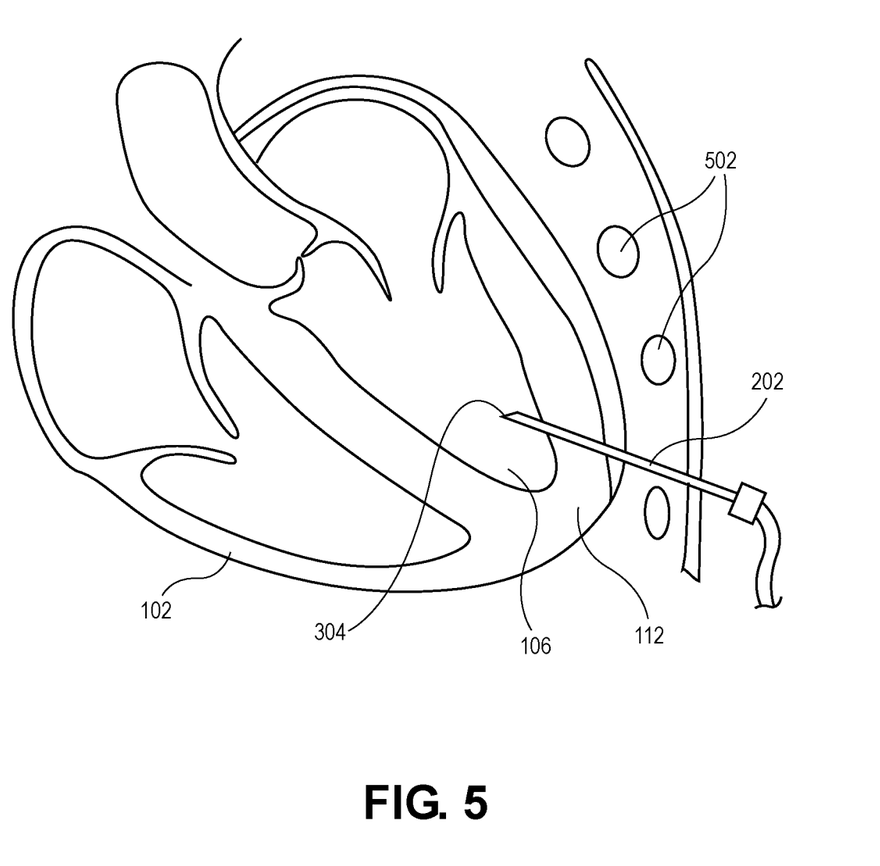
FIG. 5 is a pictorial view of a transthoracic needle accessing a left ventricle, in accordance with an embodiment.

At operation 402, the transthoracic needle 202 is inserted into the ventricle 106 of the heart 102. Referring to FIG. 5, a pictorial view of a transthoracic needle 202 accessing a left ventricle 106 is shown in accordance with an embodiment. The transthoracic needle 202 can be inserted through a rib cage 502 of the patient 100 via an intercostal puncture path. The needle can be advanced along the intercostal puncture path through the myocardium 112 of the heart 102 into the ventricle 106. In an embodiment, access to the ventricle 106 is made along a transapical path through the myocardium 112. More particularly, the transthoracic needle 202 can be inserted through the left ventricular apex located at the bottom of the left ventricle 106 to gain access to the left ventricle chamber.

The emergency medical technician can achieve precision insertion of the transthoracic needle 202 using guidance technologies. In an embodiment, the transthoracic needle 202 can be part of an ultrasound-guided puncture kit. More particularly, the emergency medical technician may use ultrasound guidance to guide the transthoracic needle 202 through the rib cage 502 into the ventricle 106. In some cases, the position of the needle can be determined visually by the guidance modality. For example, ultrasound images may be used to position the distal tip 304 of the transthoracic needle 202 at the inlet to the aorta prior to redirecting blood flow through the pump 206.

As described above, the transthoracic needle 202 can include the transthoracic needle sensor 308 to sense information about the ventricle 106. For example, the transthoracic needle sensor 308 can be a sensor and/or transducer configured to sense pressure within the ventricle 106. Such pressure information may be used by the emergency medical technician to determine appropriate needle placement. For example, the pressure sensed by the needle sensor can be monitored during puncture, and when the pressure readings indicate cyclical pressure changes, it may be determined that the transthoracic needle has accessed the ventricle 106.

At operation 404, the vascular access cannula 204 is inserted into the blood vessel 104. The blood vessel 104 can be a peripheral artery. For example, the blood vessel 104 may be a superficial femoral artery. Alternatively, the blood vessel 104 can be any peripheral artery that is accessible by standard vascular access approach in a non-hospital setting, and which can accommodate the blood flow shunted from the heart 102.

In an embodiment, the vascular access cannula 204 includes a needle, and access to the blood vessel 104 can be achieved using techniques similar to those used to access the ventricle 106. For example, ultrasound may be used to guide the vascular access cannula 204 into the artery via needle puncture.

In an embodiment, the vascular access cannula 204 includes a catheter or a cannula. Attaining vascular access can include creating a micro puncture in the blood vessel 104 using an introducer needle. A guidewire may be inserted through the introducer needle into the blood vessel 104. After guidewire access is achieved, the vessel may be dilated, e.g., by removing the introducer needle and introducing a dilator sheath over the guidewire into the blood vessel 104. The dilator may then be exchanged with the vascular access cannula 204, e.g., a catheter or cannula, to gain entry to the blood vessel 104.

At operation 406, information about the ventricular load of the heart 102 is sensed. The sensed information can include one of a heart rate, a ventricular wall stress, a systolic pressure, the diastolic pressure, or a stroke work of the ventricle 106. Such information may be sensed by a sensor or a transducer of the ventricular unloading system 200. For example, the transthoracic needle sensor 308 or a pressure sensor located along line 212 or near the inlet 208 of the pump 206 may be used to sense pressure within the ventricle 106. The pressure readings may be used to determine ventricular loading parameters directly, e.g., the systolic pressure or the diastolic pressure of the ventricle 106. Pressure readings may also be used to determine ventricular loading parameters indirectly, by analyzing the sensed information to determine corresponding data. For example, the cyclical changes in pressure can be used by the controller 220 to determine the heart rate, or the ventricular stroke work performed by the ventricle 106. The pressure readings and/or the dependent ventricular loading parameters may be used to control the pump 206, as described below.

Optionally, at operation 408, information about the vessel pressure of the blood vessel 104 is sensed. Such information may be sensed by a sensor or a transducer of the ventricular unloading system 200. For example, the vascular access cannula sensor 220 or a pressure sensor located near the outlet 210 of the pump 206 may be used to sense pressure within the blood vessel 104. The pressure readings may be used to control the pump 206, as described below.

At operation 410, the pump 206 is controlled to move blood from the transthoracic needle 202 to the vascular access cannula 204 at a pump rate. The processor(s) of the controller 220 can receive the sensed information, e.g., the information about the ventricular load and/or the information about the vessel pressure. The processor(s) can control the pump 206 based on the information. For example, the processor(s) of the controller 220 can determine and control a pump rate based on the ventricular load or the vessel pressure. Accordingly, blood can be moved from the transthoracic needle 202 disposed in the ventricle 106 to the vascular access cannula 204 disposed in the blood vessel 104 to unload the ventricle 106.

In an embodiment, the pump rate is controlled based on the ventricular load. For example, the sensed information may indicate an increase in the ventricular load. The controller 220 may control the pump 206, in response to the increase in the ventricular load, to increase the pump rate. More particularly, the controller 220 can determine how much blood to remove from the ventricle 106 based on the readings from the transthoracic needle sensor 308 (or a similar sensor in the inlet line 212 or the inlet 208) and control the pump 206 accordingly. For example, when the pressure within the ventricle 106 increases, the ventricular unloading system 200 may respond by pumping more blood from the transthoracic needle 202 to the vascular access cannula 204. By increasing the pump rate, the ventricular load can be reduced to limit infarct size.

Additionally, or alternatively, the pump rate can be controlled to ensure an appropriate pressure in the ventricle 106. For example, while reducing the ventricular load is an aim of the ventricular unloading system 200, it is contemplated that the ventricle 106 will not be completely unloaded, and that the ventricular pressure may remain high enough to circulate some blood to the vascular system, albeit at a lesser rate than would be the case if the ventricular unloading system 200 were not also circulating a portion of the blood for the ventricle 106. Accordingly, the ventricle 106 can continue to maintain organ perfusion during ventricular unloading.

In an embodiment, the flow rate through the system 200 is controlled to maintain the ventricle 106 within a normal diastolic pressure range. The range may be predetermined and set through the controller 220. For example, a target range of 6-12 mm Hg may be set as a target range, and the controller 220 can drive the pump 206 at a pump rate that maintains the pressure sensed by the sensor 222 within the target range. For example, if the sensor 222 detects a pressure above 12 mm Hg, it may indicate that the ventricle 106 is overloaded, and the pump rate can be increased to shunt more blood and off load the heart more. Alternatively, if the pressure detected by the sensor 222 falls below 6 mm Hg, it may indicate that too much blood is being shunted to allow for normal perfusion of the body through the aorta, and the pump speed can be decreased by the controller 220. Accordingly, the controller 220 can determine, based on pressure measurements from sensor(s) 222, the pump rate needed to optimally unload the ventricle 106.

In an embodiment, the pump rate is controlled based on the vessel pressure. For example, the controller 220 can control the pump rate to maintain the vessel pressure at a predetermined pressure value. The controller 220 can control the pump rate based on blood pressure feedback from the vascular access cannula sensor 220 (or a similar sensor in the outlet 210 or the outlet line 214). For example, when the blood pressure in the blood vessel 104 increases, the controller 220 can respond by reducing the pump rate to maintain the vessel pressure below a pressure threshold. Alternatively, the controller 220 can increase the pump rate to approach the pressure threshold to optimally unload the ventricle 106. Accordingly, the controller 220 may control the pump 206 based on pressure feedback from one or both of the inlet and outlet pressure sensors to balance unloading of the ventricle 106 with the appropriate pressure requirements of the blood vessel 104.

Pressure data generated by sensor 222 may also be used by the controller 220 to determine whether the transthoracic needle 202 is properly positioned. If the pressure sensor 222 located in the needle 202 or the drainage line 212 detects a sudden or abnormally high negative pressure, it may indicate that the tip 304 of the needle 202 is plugged. For example, when the needle tip 304 is withdrawn into the myocardium from the heart chamber, or if the needle tip 304 presses against the heart wall on an interior of the chamber, the cardiac tissue can plug the lumen 302. As the pump 206 continues to work to attempt to draw blood from the ventricle, a sudden or abnormal spike in negative pressure within the inlet line will occur. This sudden spike can be monitored and used to control the pump 206 accordingly. For example, in response to detecting a sudden or abnormal negative pressure spike in the inlet line, the controller 220 can pause pumping and display a notification alerting the user to reposition the needle 202 within the ventricle 106 before resuming pumping.

Figure 6:
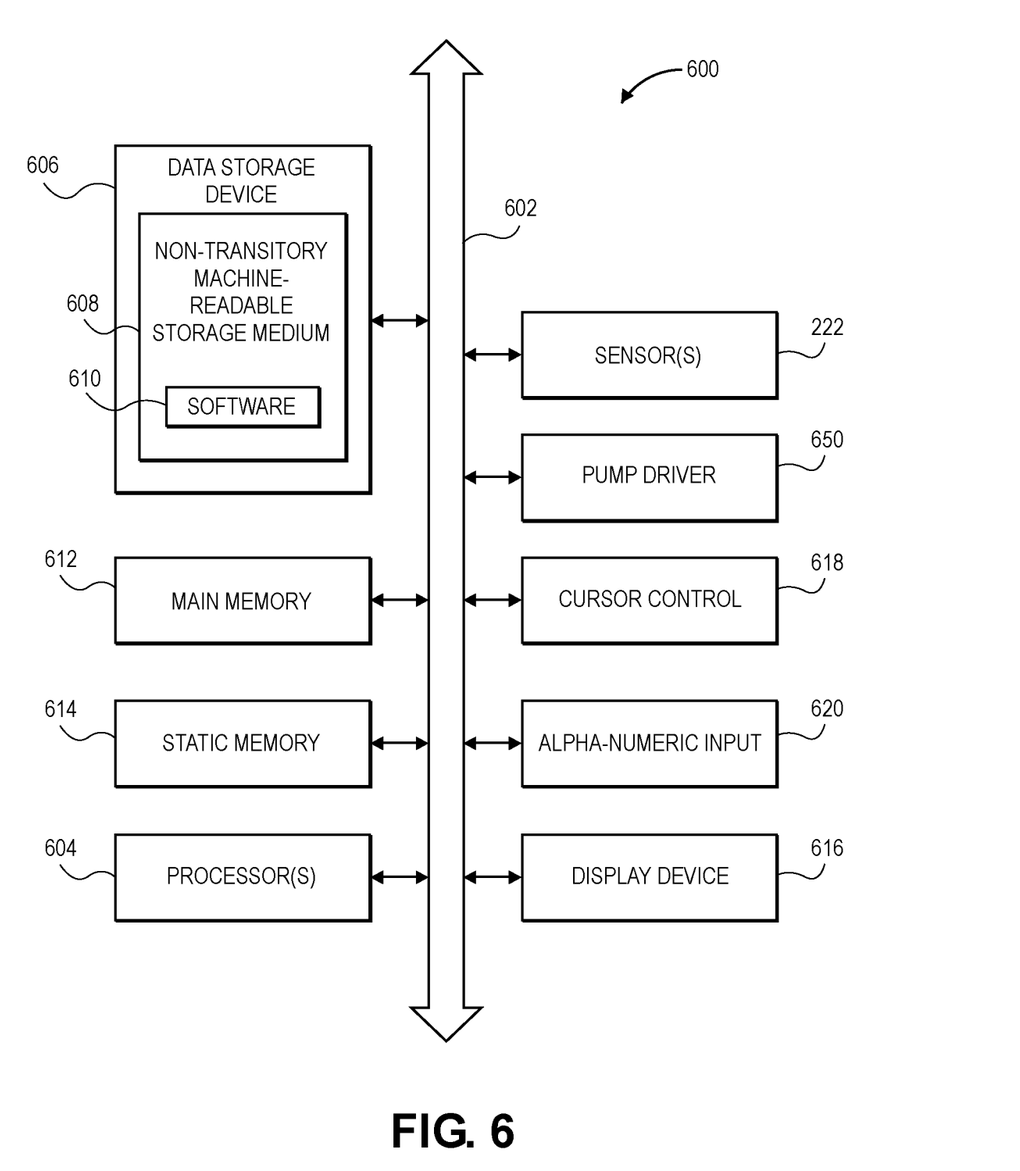
FIG. 6 is a diagram of components of a ventricular unloading system, in accordance with an embodiment.

Referring to FIG. 6, a diagram of components of a ventricular unloading system is shown in accordance with an embodiment. The ventricular unloading system 200 includes a computer system 600 having one or more of the components shown, and the components may be interconnected in any manner. More particularly, the computer system 600 can have fewer or more components than shown. Furthermore, the computer system 600 may be integrated with another component of the ventricular unloading system 200. For example, the computer system 600 may be contained within the housing of the console 207 that also houses the pump 206 to provide a compact, mobile unit that has a small footprint and can be easily stored and transported by emergency medical personnel.

In an embodiment, the computer system 600, which is a form of data processing system, includes a bus 602 that is coupled to one or more processors 604. The bus 602 may also be coupled to a data storage device 606, which can include memory. For example, the data storage device 606 can include a non-transitory computer-readable storage medium 608. The non-transitory computer-readable storage medium 608 can store instructions, e.g., software 610, which when executed by the one or more processors 604 of the ventricular unloading system 200 causes the ventricular unloading system 200 to perform any of the methods or method operations described above. The computer system 600 may include main memory 612, which may include random access memory, and/or static memory 614, which may include read only memory. Any of these memory devices can store the instructions, which when executed by the one or more processors 604 of the ventricular unloading system 200 causes the ventricular unloading system 200 to perform any of the methods or method operations described above.

The bus 602 can connect the processor(s) 604 and the memory components to various input and output components. In an embodiment, sensor(s) 222 including the transthoracic needle sensor 308 or the vascular access cannula sensor 220 described above can be interconnected with the processor(s) 604 and memory to provide sensed information to the components. The sensed information may be used by the processor(s) 604 to determine parameters, such as ventricular load or pump rate, and to control the pump 206 accordingly. More particularly, the processor(s) 604 can be interconnected with a pump driver 650. The pump driver 650 can be a motor driver that acts as an interface between the motor portion of the pump 206 and the control circuitry of the computer system 600, e.g., the processor(s) 604. The pump driver 650 can connect to and drive the motor portion of the pump 206 to drive the pump portion of the pump 206. Accordingly, the computer system 600 can drive the pump 206 to control the pump rate and move blood from the ventricle to the blood vessel during ventricular unloading.

The bus 602 can connect the processor(s) 604 to a display controller and a display device 616 to present information about the vascular unloading procedure to the emergency medical personnel. For example, the display can present a visual display of pressure data, images related to needle position, or other information that is useful to the performance of the procedure. The display device 616 can be integrated in the console 207 and/or may be a display of a remote device, e.g., a tablet computer, in communication with the bus 602 via a wired or wireless connection. The processor(s) 604 can also connect through the bus 602 to peripheral devices such as input/output devices, including a cursor control 618 such as a mouse, or an alpha-numeric input 620 such as a keyboard.

Using the ventricular unloading system described above, emergency medical personnel can safely and quickly unload the ventricle during and after a heart attack. The treatment may be performed based on detection of oxygen supply and/or demand of the myocardium to match the ventricular load with the blood supply. The treatment can provide an early defense against AMI to effectively mitigate myocardial damage caused by the heart attack. More particularly, by unloading the ventricle early on in a non-hospital setting, a reduction of infarct size of 10% can be expected, and clinical outcomes can be improved.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A ventricular unloading system, comprising:
    a transthoracic needle having a needle point and a proximal hub, wherein the transthoracic needle includes the needle point and a rigid, thin-walled hypotube structure adapted to access a ventricle of a heart transthoracically and is sized such that the proximal hub is located outside of a chest wall when the needle point is inserted transthoracically through the chest wall via puncture along an intercostal path or a transapical path into the ventricle of the heart;
    a vascular access cannula;
    a pump including an inlet coupled to the transthoracic needle and an outlet coupled to the vascular access cannula; and
    a controller including one or more processors configured to receive sensed information about a ventricular load of the heart, and control the pump, based on the sensed information, to move blood from the proximal hub of the rigid transthoracic needle when the needle point is disposed in the ventricle of the heart to the vascular access cannula disposed in a blood vessel.

2. The ventricular unloading system of claim 1, wherein the sensed information includes one of a heart rate, a ventricular wall stress, a systolic pressure, a diastolic pressure, or a stroke work of the ventricle.

3. The ventricular unloading system of claim 1, wherein the sensed information indicates an increase in the ventricular load, and wherein controlling the pump includes increasing a pump rate in response to the increase in the ventricular load.

4. The ventricular unloading system of claim 1, wherein the transthoracic needle includes a transthoracic needle sensor to sense the information about the ventricular load.

5. The ventricular unloading system of claim 1, wherein the one or more processors are further configured to receive sensed information about a vessel pressure of the blood vessel, and control the pump based on the vessel pressure.

6. The ventricular unloading system of claim 5, wherein controlling the pump based on the vessel pressure includes controlling a pump rate to maintain the vessel pressure at a predetermined pressure value.

7. The ventricular unloading system of claim 5, wherein the vascular access cannula includes an access cannula sensor to sense the information about the vessel pressure.

8. The ventricular unloading system of claim 1, wherein the pump is a peristaltic pump.

9. A method, comprising:
inserting a needle point of a transthoracic needle transthoracically through a chest wall via puncture along an intercostal path or a transapical path into a ventricle of a heart, wherein the transthoracic needle includes the needle point and a rigid, thin-walled hypotube structure adapted to access the ventricle of the heart transthoracically and is sized such that a proximal hub of the transthoracic needle is located outside of the chest wall when the needle point is in the ventricle of the heart;
inserting a vascular access cannula into a blood vessel;
sensing information about a ventricular load of the heart; and
controlling a pump having an inlet connected to the transthoracic needle and an outlet connected to the vascular access cannula, wherein the pump is controlled, based on the sensed information, to move blood from the proximal hub of the rigid transthoracic needle when the needle point is disposed in the ventricle to the vascular access cannula disposed in the blood vessel.

10. The method of claim 9, wherein the sensed information includes one of a heart rate, a ventricular wall stress, a systolic pressure, a diastolic pressure, or a stroke work of the ventricle.

11. The method of claim 9, wherein the sensed information indicates an increase in the ventricular load, and wherein controlling the pump includes increasing a pump rate in response to the increase in the ventricular load.

12. The method of claim 9, further comprising:
sensing information about a vessel pressure in the blood vessel; and
controlling the pump based on the vessel pressure.

13. The method of claim 12, wherein controlling the pump based on the vessel pressure includes controlling a pump rate to maintain the vessel pressure at a predetermined pressure value.

14. The method of claim 9, wherein inserting the transthoracic needle into the ventricle includes guiding the transthoracic needle through a rib cage into the ventricle using ultrasound guidance.

15. A non-transitory computer-readable medium storing instructions which, when executed by one or more processors of a ventricular unloading system, cause the ventricular unloading system to perform a method comprising:
receiving, by the one or more processors of the ventricular unloading system, sensed information about a ventricular load of a heart; and
controlling, by the one or more processors, a pump having an inlet connected to a transthoracic needle and an outlet connected to a vascular access cannula, wherein the transthoracic needle has a needle point and a rigid, thin-walled hypotube structure adapted to access a ventricle of the heart transthoracically and is sized such that the proximal hub is located outside of a chest wall when the needle point is inserted transthoracically through the chest wall via puncture along an intercostal path or a transapical path into the ventricle of the heart, and wherein the pump is controlled based on the sensed information to move blood from the proximal hub of the rigid transthoracic needle when the needle point is disposed in the ventricle of the heart to a vascular access cannula disposed in a blood vessel.

16. The non-transitory computer-readable medium of claim 15, wherein the sensed information includes one of a heart rate, a ventricular wall stress, a systolic pressure, a diastolic pressure, or a stroke work of the ventricle.

17. The non-transitory computer-readable medium of claim 15, wherein the sensed information indicates an increase in the ventricular load, and wherein controlling the pump includes increasing a pump rate in response to the increase in the ventricular load.

18. The non-transitory computer-readable medium of claim 15, the method further comprising:
receiving, by the one or more processors, sensed information about a vessel pressure in the blood vessel; and
controlling, by the one or more processors, the pump based on the vessel pressure.

19. The non-transitory computer-readable medium of claim 18, wherein controlling the pump based on the vessel pressure includes controlling a pump rate to maintain the vessel pressure at a predetermined pressure value.

* * * * *